United States Patent [19]

Christensen

[11] Patent Number: Plant 7,658

[45] Date of Patent: Oct. 1, 1991

[54] ROSE PLANT JACLAV

[75] Inventor: Jack Christensen, Ontario, Calif.

[73] Assignee: Bear Creek Gardens, Inc., Medford, Oreg.

[21] Appl. No.: 520,661

[22] Filed: May 8, 1990

[51] Int. Cl.[5] ..... A01H 5/00

[52] U.S. Cl. ..... Plt./11

[58] Field of Search ..... Plt. 11, 1, 18, 19, Plt./20, 22, 26, 27, 28

*Primary Examiner*—Howard J. Locker

*Attorney, Agent, or Firm*—Klarquist, Sparkman, Campbell, Leigh & Whinston

[57] ABSTRACT

A hybrid tea class rose plant having cutting stems averaging 24 inches, excellent flower production for the lavender group or roses, averaging 25 to 27 cut stems per plant per year, distinctive red-purple color of flowers, heavy scent, and unusual green young foliage with red-purple undersides.

1 Drawing Sheet

1

The present invention relates to a new and distinct variety of rose plant of the hybrid tea class which was originated by me by crossing an unnamed breeding line with the variety Shocking Blue.

The primary objective of this breeding was to produce a new rose variety having the flower color and glossy foliage of the male parent, Shocking Blue, combined with the long stems and excellent vigor of the female breeding line. The objective was substantially achieved along with other desirable improvements as evidenced by the following unique combination of characteristics which are outstanding in the new variety and which distinguish it from its parents as well as from all other varieties of which I am aware:

1. Long cutting stems—average 24 inches.
2. Excellent cut flower production for the lavender group of cut roses. Production is 25–27 stems per plant per year.
3. Distinctive red-purple color of flowers.
4. Heavy scent.
5. Unusual green color with red-purple underside on young foliage.

Asexual reproduction of this new variety by budding, as performed at Somis, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color terminology in accordance with The Royal Horticultural Society (London) Colour Chart, except were ordinary dictionary significance of color is indicated.

Parentage:

*Seed parent.*—An unnamed breeding line.

*Pollen parent.*—Shocking Blue.

Classification:

*Botanical.*—*Rosa hybrida.*

*Commercial.*—Hybrid tea.

2

FLOWER

Observations made from specimens grown in a greenhouse environment in Bear Creek Gardens greenhouse, Somis, Calif., in Jan. 1990.

Blooming habit: Recurrent.

Bud:

*Size.*—About 1½ inches long when the petals start to unfurl.

*Form.*—The bud form is long, pointed ovoid.

*Color.*—When sepals first divide, the bud color is Red-Purple Group 60C. This changes rapidly to Red-Purple Group 63C when the petals are fully reflexed. When half blown, the upper and lower sides of the petals are Red-Purple Group 63B to C.

*Sepals.*—Color: Green Group 139B. Surface texture: Covered with fine hairs. There are three normally appendaged sepals. There are two unappendaged sepals with hairy edges.

*Receptacle.*—Color: Green Group 143A. Shape: Funnel. Size: Small. For such a large flower, there is very little swelling where the peduncle meets the flower (the receptacle). Surface: Smooth.

*Peduncle.*—Length, averaging about 6 inches. Surface: Pickly, many small prickles that are pale green. Color: Light green. Strength: Stiff, erect.

Bloom:

*Size.*—Large. Average open diameter is 4½ to 5 inches.

*Borne.*—Singly.

*Stems.*—Long, average 24 inches or longer.

*Form.*—When first open, bloom has a high center. Bloom retains its form to the end, and outer petals curl back.

*Petalage.*—Number of petals under normal conditions: 30.

*Color.*—The upper and reverse sides of the petals are Red-Purple Group 63B to C. The base of petals has a small yellow half moon at the point of attachment (¼ inch × ¼ inch). The major color on the upper side is Red-Purple Group 63B.

*Variegations.*—Occasional white streak on the guard petals.

*Discoloration.*—No general tonality change at the end of the first day and at the end of the third day.

*Fragrance.*—Strong.

Petals:

*Texture.*—Thick.

*Shape.*—Round to deltoid.

*Form.*—Tips slightly recurved.

*Arrangement.*—Imbricated, with few petaloids in the center.

*Persistence.*—Petals drop off cleanly before drying.

*Lastingness.*—On the plant: Long, about 5 to 7 days. As a cut flower: Long, about 7 days.

Reproductive parts:

*Anthers.*—Size: Large. Quantity: Many. Color: Yellow. Arrangement: Regular around styles.

*Filaments.*—Color: White.

*Pollen.*—Color: Lemon yellow.

*Styles.*—Color: Red.

*Stigmas.*—Color: Yellow.

Plant form: Bush.

Plant growth: Very vigorous, upright, branching.

Foliage:

*Number of leaflets on normal mid-stem leaves.*—5 or 7.

*Size.*—Very large, mature leaf is about 6½ to 7 inches long.

*Quantity.*—Abundant.

*Color.*—New foliage is bronze, especially on leaf underside. Top of leaf turns green very rapidly while underside stays reddish bronze for up to two weeks before it turns green. Old foliage is dark glossy green.

Leaflets:

*Shape.*—Pointed oval.

*Texture.*—Upper side: Leathery, glossy.

*Edge.*—Serrated.

*Serration.*—Single, small.

*Petiole rachis.*—Color: Reddish.

*Petiole underside.*—Rough, with prickles.

*Stipules.*—Medium, about ½ inch long, bearded.

*Disease resistance.*—Resistant to mildew under normal growing conditions at Somis, Calif. Because this is a greenhouse cut flower rose, it has not been grown outside and therefore has not been exposed to either rust or blackspot. No determination has been made on susceptibility or resistance to these pathogens.

Wood:

*New wood.*—Color: Reddish. Bark: Smooth.

*Old wood.*—Color: Green. Bark: Smooth.

Prickles:

*Quantity.*—Ordinary quantity on main canes from base and on laterals from main canes.

*Form.*—Medium to short—about ¼ inch long, straight.

*Color when young.*—Red, brown.

Small prickles:

*Quantity.*—None on main stalks and on laterals.

I claim:

1. A new and distinct variety of rose plant of the hybrid tea class, substantially as herein shown and described, characterized particularly as to novelty by the unique combination of its high annual cut flower production, long cutting stems, unusual red-purple color of blooms, strong fragrance, and unusual colored young foliage.

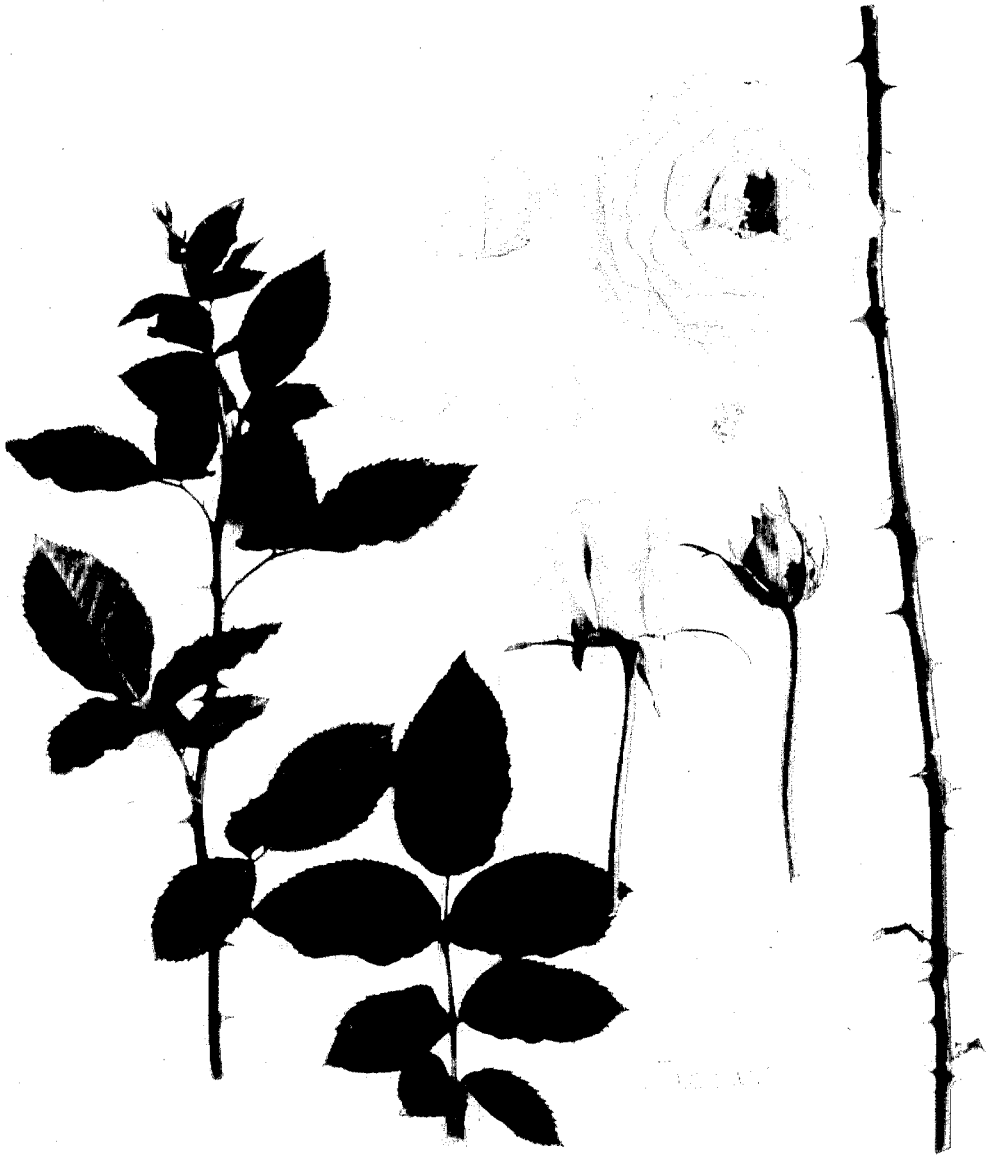

* * * * *